US007070939B2

(12) United States Patent
Montgomery et al.

(10) Patent No.: US 7,070,939 B2
(45) Date of Patent: Jul. 4, 2006

(54) METHODS FOR DETECTING VASCULOPATHIES AND TUMORS

(75) Inventors: Anthony Montgomery, San Diego, CA (US); Paul Demarco, Wausau, WI (US); Fang Mei, League City, TX (US)

(73) Assignee: The Scripps Research Institute, La Jolla, CA (US)

( * ) Notice: Subject to any disclaimer, the term of this patent is extended or adjusted under 35 U.S.C. 154(b) by 131 days.

(21) Appl. No.: 10/130,085

(22) PCT Filed: Sep. 26, 2001

(86) PCT No.: PCT/US01/30317

§ 371 (c)(1), (2), (4) Date: Apr. 28, 2003

(87) PCT Pub. No.: WO02/29404

PCT Pub. Date: Apr. 11, 2002

(65) Prior Publication Data

US 2003/0215389 A1   Nov. 20, 2003

Related U.S. Application Data

(60) Provisional application No. 60/237,554, filed on Oct. 2, 2000.

(51) Int. Cl.
*G01N 33/53* (2006.01)
*C12Q 1/68* (2006.01)
*C07K 14/00* (2006.01)
*C07K 16/00* (2006.01)

(52) U.S. Cl. .................... 435/7.1; 435/6; 530/350; 530/387.1

(58) Field of Classification Search .............. 435/6, 435/7.1, 69.1; 530/387.1, 350; 424/130.1, 424/143.1

See application file for complete search history.

(56) References Cited

U.S. PATENT DOCUMENTS 3,464,890 A   9/1969   Weichselbaum .............. 195/66

(Continued)

FOREIGN PATENT DOCUMENTS

EP   0572664   12/1999

(Continued)

OTHER PUBLICATIONS

Ong et al., "Serum neural adhesion molecule differentiates multiple myeloma from paraproteinemias due to other causes," Blood 87(2):712-718, 1996.*

(Continued)

*Primary Examiner*—Robert A. Wax
*Assistant Examiner*—Rosanne Kosson
(74) *Attorney, Agent, or Firm*—Morrison & Foerster LLP (57) ABSTRACT

This invention relates generally to the field of prognosis and diagnosis of vasculopathy and certain tumors. In particular, the invention provides a method for prognosing or diagnosing vasculopathy, neuroectodermal tumor, epithelial tumor, myelomonocytic tumor or lymphoid tumor in a mammal, which method comprises: a) assessing a NCAM L1 protein or a derivative or fragment thereof, or a mRNA encoding said NCAM L1 protein or a derivative or fragment thereof, in a mammal having or suspected of having vasculopathy, neuroectodermal tumor, epithelial tumor, lymphoid tumor or myelomonocytic tumor; b) assessing a NCAM L1 protein or a derivative or fragment thereof, or a mRNA encoding said NCAM L1 protein or a derivative or fragment thereof, in a mammal not having said vasculopathy, neuroectodermal tumor, epithelial tumor, lymphoid tumor or myelomonocytic tumor; c) comparing the presence or quantity of said NCAM L1 protein or mRNA assessed in steps a) and b), whereby said NCAM L1 protein or mRNA assessed in step a) is more than that assessed in step b) indicates the presence of said vasculopathy, neuroectodermal tumor, epithelial tumor, lymphoid tumor or myelomonocytic tumor in said mammal. The method can also be used for monitoring the effectiveness of the treatment of the vasculopathy, neuroectodermal tumor, epithelial tumor, lymphoid tumor or myelomonocytic tumor.

8 Claims, 3 Drawing Sheets

U.S. PATENT DOCUMENTS

| | | | |
|---|---|---|---|
| 3,647,070 A | 3/1972 | Adler | 210/83 |
| 3,780,935 A | 12/1973 | Lukacs et al. | 233/1 A |
| 3,852,194 A | 12/1974 | Zine, Jr. | 210/83 |
| 4,140,631 A | 2/1979 | Okuda et al. | 210/83 |
| 4,477,575 A | 10/1984 | Vogel et al. | 436/170 |
| 4,803,153 A | 2/1989 | Shibata et al. | 435/2 |
| 5,364,533 A | 11/1994 | Ogura et al. | 210/645 |
| 5,969,124 A | 10/1999 | Lemmon | 536/23.5 |

FOREIGN PATENT DOCUMENTS

| | | |
|---|---|---|
| WO | WO 98/36062 | 8/1998 |
| WO | WO-02/04952 A2 | 1/2002 |

OTHER PUBLICATIONS

Disease Information Fact Sheet 17, The chronic myelomonocytic leukemias (CMML), The Leukemia & Lymphoma Society, http://www.leukemia-lymphoma.org/all_mat_toc.adp?item_id=69974&cat_id=1215, downloaded on Nov. 9, 2004.*

Aunoble et al. "Major Oncogenes and Tumor Suppressor Genes Involved in Epithelial Ovarian Cancer (Review)" Int. J. Oncol. 16(3): 567-576 (2000).

Bergers et al. "Extrinsic Regulators of Epithelial Tumor Progression: metalloproteinases" Curr. Opin. Genet. Dev. 10(1): 120-127 (2000).

Ching et al. "CT and MR Imaging Appearances of an Extraosseous Calcifying Epithelial Odontogenic Tumor (Pindborg Tumor)" Am. J. Neuroradiol. 21(2): 343-345 (2000).

De Alava et al. "Molecular Biology of the Ewing's Sarcoma/Primitive Neuroectodermal Tumor Family" J. Clin. Oncol. 18(1): 204-213 (2000).

De Souza et al. "Cell Cycle-Associated Proteins in Melanotic Neuroectodermal Tumor of Infancy".

Ferrara et al. "CD56 Expression Is an Indicator of Poor Clinical Outcome in Patients with Acute Promyelocytic-Leukemia Treated with Simultaneous All-Trans-Retinoic Acid and Chemotherapy" J. Clin. Oncol. 18(6):1295-1300 (2000).

Hage et al. "Neural Cell Adhesion Molecule Expression" Chest 114: 1316-1320 (1998).

Jennette et al. "Small-Vessel Vasculititis" N. Engl. J. Med. 337(21):1512-1523 (1997).

Kaya et al. "Melanotic Neuroectodermal Tumor of Infancy Report of Two Cases and Review of Literature" Int. J. Pediatr. Otorhinolaryngol. 52(2):169-172 (2000).

Kiratli et al. "Primitive Neuroectodermal Tumor of the Orbit in an Adult" Ophthalmology 106(1): 98-102 (1999).

Komminoth et al. "Overlapping Expression of Immunohistochemical Markers and Synaptophysin mRNA in Pheochromocytomas and Adrenocortical Carcinomas" Laboratory Investigation 72(4):424-431 (1995).

Lieutaud et al. "Renal and Adrenal Gland Localization of Chronic Myelomonocytic Leukemia Presenting as a Kidney Tumor" Leuk. Lymphoma 34(3-4): 405-408 (1999).

Mat et al. "Small Vessel Vasculitis and Vasculitis Confined to Skin" Baillieres Clin. Rheumatol. 11(2): 237-257 (1997).

Moos et al. "Neural Adhesion Molecule L1 as a Member of the Immunoglobulin Superfamily with Binding Domains Similar to Fibronectin" Nature 334: 701-703 (1988).

Ong et al. "Serum Neural Cell Adhesion Molecule Differentiates Multiple Myeloma from Paraproteinemias Due to Other Causes" Blood 87(2):712-716 (1996).

Toda et al. "Primitive Neuroectodermal Tumor in Sinonasal Region" Auris Nasus Larynx 26(1): 83-90 (1999).

Watson et al. *Molecular Biology of the Gene* 4th Ed. The Bejacmin/Cummings Pub. Co. p. 224 (1987).

Allory et al., Clinical Cancer Research (2005) 11:1190-1197.

Calvo et al., Cancer Research (2002) 62:5325-5335.

Figarella-Branger et al., Cancer Research (1990) 50:6364-6370.

Fogel et al., The Lancet (2003) 362:869-875.

Gavert et al., The Journal of Cell Biology (2005) 168(4):633-642.

Katayama et al., Cell Structure and Function (1997) 22:511-516.

Meli et al., Int. J. Cancer (1999) 83:401-408.

Montgomery et al., The Journal of Cell Biology (1996) 132(3):475-485.

Mujoo et al., The Journal of Biological Chemistry (1986) 261(22):10299-10305.

Primiano et al., Cancer Cell (2003) 4:41-53.

Suzuki et al., J. Clin. Pathol. (2005) 58:166-171.

Thies et al., European Journal of Cancer (2002) 38:1708-1716.

* cited by examiner

METHODS FOR DETECTING VASCULOPATHIES AND TUMORS

This appln. claims the benefit of 60/237,554, filed Oct. 2, 2000.

This invention was made with government support under Contract No. NIH CA 69112-01 by the National Institutes of Health. The government has certain rights to this invention.

TECHNICAL FIELD

This invention relates generally to the field of prognosis and diagnosis of vasculopathy and certain tumors. In particular, the invention provides a method for prognosing or diagnosing vasculopathy, neuroectodermal tumor, epithelial tumor, myelomonocytic tumor or lymphoid tumor in a mammal, which method comprises: a) assessing a NCAM L1 protein or a derivative or fragment thereof, or a mRNA encoding said NCAM L1 protein or a derivative or fragment thereof, in a mammal having or suspected of having vasculopathy, neuroectodermal tumor, epithelial tumor, lymphoid tumor or myelomonocytic tumor; b) assessing said NCAM L1 protein or a derivative or fragment thereof, or said mRNA encoding said NCAM L1 protein or a derivative or fragment thereof, in a mammal not having said vasculopathy, neuroectodermal tumor, epithelial tumor, lymphoid tumor or myelomonocytic tumor; and c) comparing the presence or quantity of said NCAM L1 protein or mRNA assessed in steps a) and b), whereby said NCAM L1 protein or mRNA assessed in step a) is more than that assessed in step b) indicates the presence of said vasculopathy, neuroectodermal tumor, epithelial tumor, lymphoid tumor or myelomonocytic tumor in said mammal. The method can also be used for monitoring the effectiveness of the treatment of the vasculopathy, neuroectodermal tumor, epithelial tumor, lymphoid tumor or myelomonocytic tumor.

BACKGROUND ART

Small vessel vasculitis can exist in various forms such as cutaneous vasculitis, urticarial vasculitis, leukocytoclastic vasculitis, livedo vasculitis and nodular vasculitis (See generally, Jennette and Falk, *N. Engl. J. Med.*, 337(21):1512–23 (1997)). Some small vessel vasculitis, e.g., cutaneous vasculitis, is a heterogeneous group of disorders, which can be confined to the skin or may be part of an associated systemic disease (Mat et al., *Baillieres Clin. Rheumatol.*, 11(2): 237–57 (1997)). Various aetiological agents as well as conditions that mimic skin vasculitis, usually present with similar clinical features; mainly palpable purpura. The skin biopsies usually show leukocytoclastic vasculitis. This poses a great diagnostic and therapeutic challenge for the physician.

Certain tumors, such as neuroectodermal tumor, epithelial tumor or myelomonocytic tumor, also exist in various forms (See e.g., Kaya et al., *Int. J. Pediatr. Otorhinolaryngol.*, 52(2):169–72 (2000); de Alava and Gerald, *J. Clin. Oncol.*, 18(1):204–13 (2000); de Souza et al., *Oral Surg. Oral Med. Oral Pathol. Oral Radiol. Endod.*, 88(4):466–8 (1999); Toda et al., *Auris Nasus Larynx*, 26(1):83–90 (1999); Kiratli et al., *Ophthalmology*, 106(1):98–102 (1999); Ching et al., *Am. J. Neuroradiol.*, 21(2):343–5 (2000); Bergers and Coussens, *Curr. Opin. Genet. Dev.*, 10(1):120–7 (2000); Aunoble et al., *Int. J. Oncol.*, 16(3):567–76 (2000); and Lietuaud et al., *Leuk. Lymphoma.*, 34(3–4):405–8 (1999)).

Therefore, it is an object of the present invention to provide methods for prognosing or diagnosing vasculopathy, neuroectodermal tumors, epithelial tumors and myelomonocytic tumors.

DISCLOSURE OF THE INVENTION

This invention relates generally to the field of prognosis and diagnosis of vasculitises and certain tumors. In one aspect, the invention is directed to a method for prognosing or diagnosing a vasculopathy in a mammal, which method comprises: a) assessing a NCAM L1 protein or a derivative or fragment thereof, or a mRNA encoding said NCAM L1 protein or a derivative or fragment thereof, in a mammal having or suspected of having a vasculopathy; b) assessing said NCAM L1 protein or a derivative or fragment thereof, or said mRNA encoding said NCAM L1 protein or a derivative or fragment thereof, in a mammal not having said vasculopathy; and c) comparing the presence or quantity of said NCAM L1 protein or mRNA assessed in steps a) and b), whereby said NCAM L1 protein or mRNA assessed in step a) is more than that assessed in step b) indicates the presence of said vasculopathy in said mammal. The method can also be used for monitoring the effectiveness of the treatment of the vasculopathy.

In another aspect, the invention is directed to a method for prognosing or diagnosing a neuroectodermal, epithelial, myelomonocytic or lymphoid tumor in a mammal, which method comprises: a) assessing a NCAM L1 protein or a derivative or fragment thereof, or a mRNA encoding said NCAM L1 protein or a derivative or fragment thereof, in a mammal having or suspected of having a neuroectodermal, epithelial, myelomonocytic or lymphoid tumor; b) assessing said NCAM L1 protein or a derivative or fragment thereof, or said mRNA encoding said NCAM L1 protein or a derivative or fragment thereof, in a mammal not having said neuroectodermal, epithelial myelomonocytic or lymphoid tumor; and c) comparing the presence or quantity of said NCAM L1 protein or mRNA assessed in steps a) and b), whereby said NCAM L1 protein or mRNA assessed in step a) is more than that assessed in step b) indicates the presence of said neuroectodermal, epithelial, myelomonocytic or lymphoid tumor in said mammal. The method can also be used for monitoring the effectiveness of the treatment of the neuroectodermal, epithelial, myelomonocytic or lymphoid tumor.

BRIEF DESCRIPTION OF THE DRAWINGS

FIG. 1 depicts an enzyme-linked iemmunoabsorbent assay to detect L1 in serum. Plates were coated with anti-L1 MAb 5G3 and were blocked with 5% BSA. The wells were then incubated with diluted serum samples (1 in 10 in PBS). After washing, the wells were incubated with an affinity purified anti-L1 rabbit polygonal antibody. Bound rabbit antibody was detected using a human absorbed goat anti-rabbit IgG horseradish peroxidase conjugate. (A) A titration of the recombinant L1-ECD was added to some wells (0.1–5 ng/ml) to generate a standard curve. (B) A scatter plot of results obtained from serum samples from normal individuals or patients with autoimmune diseases with or without evidence of vascular disease. Serum samples were obtained from patients with rheumatoid arthritis (RA), large or small vessel vasculitis, lupus (SLE) with or without small vessel vasculitis, and from patients with scleroderma. It is important to note that substitution of either MAb 5G3 or the anti-L1 polyclonal antibody with isotype matched monoclonal or control polyclonal antibody prevented any reactivity and that no evidence was found for reactivity with human immunoglobulin.

FIG. 2 depicts vascular L1-expression. A & B. Normal skin stained with an isotype matched control MAb (A), or with anti-L1 MAb 5G3 (B). C. Psoriatic skin stained with MAb 5G3. D&E. Skin from a patient with small vessel vasculitis stained with control MAb (D), or with MAb 5G3 (E). F&G. Synovial tissue from patients with rheumatoid arthritis stained with MAb 5G3. H. Synovial tissue stained for double immunofluorescence using 5G3 (red) and an anti-PECAM MAb (green). Samples were snap frozen and the sections fixed with acetone and blocked prior to antibody staining.

MODES OF CARRYING OUT THE INVENTION

A. Definitions

Unless defined otherwise, all technical and scientific terms used herein have the same meaning as is commonly understood by one of ordinary skill in the art to which this invention belongs. All patents, applications, published applications and other publications and sequences from GenBank and other databases referred to herein are incorporated by reference in their entirety.

As used herein, "vasculopathy" refers to any disease of the blood vessels.

As used herein, "vasculitis (angiitis or angitis)" refers to inflammation of a blood vessel, e.g., arteritis, phlebitis, or lymphatic vessel, e.g., lymphangitis. Vasculitis can take various forms such as cutaneous vasculitis, urticarial vasculitis, leukocytoclastic vasculitis, livedo vasculitis and nodular vasculitis.

As used herein, "small vessel vasculitis" refers to inflammation of small or medium sized blood or lymphatic vessel, e.g., capillaries, venules, arterioles and arteries.

As used herein, "cutaneous (or hypersensitivity) vasculitis" refers to an acute form of vasculitis that may affect the skin only, but also may involve other organs, with a polymorphonuclear infiltrate in the walls of and surrounding small (dermal) vessels. Nuclear fragments are formed by karyorrhexis of the neutrophils.

As used herein, "leukocytoclastic vasculitis" refers to cutaneous acute vasculitis characterized clinically by palpable purpura, especially of the legs, and histologically by exudation of the neutrophils and sometimes fibrin around dermal venules, with nuclear dust and extravasation of red cells; may be limited to the skin or involve other tissues as in Henoch-Schönlein purpura.

As used herein, "urticarial (or hypocomplementemic) vasculitis" refers to painful, purpuric cutaneous lesions resembling urticaria but lasting more than 24 hours, with biopsy findings of leukocytoclastic vasculitis and variable systemic changes, often with hypocomplementemia.

As used herein, "livedo vasculitis" refers to hyaline degeneration of the walls of small dermal blood vessels with thrombolic occlusion seen with cryoglobulinemia or in atrophic blanche. No necrosis is seen.

As used herein, "nodular vasculitis" refers to chronic or recurrent nodular lesions of subcutaneous tissue, especially of the legs of older women, with lobular panniculitis, granulomatous inflammation with multinucleated giant cells, focal necrosis, and obliterative inflammation of the small blood vessels, resembling erythema induratum but without evidence of associated tuberculosis.

As used herein, "Wegener's granulomatosis" refers to granulomatous inflammation involving the respiratory tract and necrotizing vasculitis affecting small to medium-sized vessels, e.g., capillaries, venules, arterioles, and arteries. Necrotizing glomerulonephritis is common in patients with Wegener's granulomatosis.

As used herein, "Churg-Strauss syndrome" refers to eosinophil-rich and granulomatous inflammation involving the respiratory tract and necrotizing vasculitis affecting small to medium-sized vessels and associated with asthma and blood eosinophilla.

As used herein, "microscopic polyangitis (microscopic polyarteritis)" refers to necrotizing vasculitis with few or no immune deposits affecting small vessels, i.e., capillaries, venules, or arterioles. Necrotizing arteritis involving small and medium-sized arteries may be present in patients with microscopic polyangiitis. Necrotizing glomerulonephritis is common. Pulmonary capillaritis often occurs.

As used herein, "Henoch-Schönlein purpura" refers to vasculitis with IgA-dominant immune deposits affecting small vessels, i.e., capillaries, venules, or arterioles. Henoch-Schönlein purpura typically involves skin, gut, and glomerull and associated with arthralgias or arthritis.

As used herein, "essential cryoglobulinemic vasculitis" refers to vasculitis with cryoglobulin immune deposits affecting small vessels, i.e., capillaries, venules, or arterioles, and associated with cryoglobulins in serum. Skin and glomerull are often involved in essential cryoglobulinemic vasculitis.

As used herein, "cutaneous leukocytoclastic angiitis" refers to isolated cutaneous leukocytoclastic angiitis without system vasculitis or glomerulonephritis.

As used herein, "polyarteritis nodosa (classic polyarteritis nodosa)" refers to necrotizing inflammation of medium-sized or small arteries without glomerulonephritis or vasculitis in arterioles, capillaries, or venules.

As used herein, "Kawasaki disease" refers to arteritis involving large, medium-sized and small arteries and associated with mucocutaneous lymph node syndrome. Coronary arteries are often involved, and aorta and veins may be involved in Kawasaki disease. Kawasaki disease usually occurs in children.

As used herein, "giant cell (temporal) arteritis" refers to granulomatous arteritis of the aorta and its major branches, with a predilection for the extracranial branches of the carotid artery. Gian cell (temporal) arteritis often involves the temporal artery. Usually occurs in patients older than 50 and often is associated with polymyalgia rheumatica.

As used herein, "Takayasu's arteritis" refers to granulomatous inflammation of the aorta and its major branches. It usually occurs in patients younger than age 50.

As used herein, "neoplasm (neoplasia)" refers to abnormal new growth, and thus means the same as tumor, which may be benign or malignant. Unlike hyperplasia, neoplastic proliferation persists even in the absence of the original stimulus.

As used herein, "cancer" refers to a general term for diseases caused by any type of malignant tumor.

As used herein, "neuroectodermal tumor" refers to a tumor or cancer that is present and/or originated from neuroectoderm.

As used herein, "epithelial tumor" refers to a tumor or cancer that is present and/or originated from epithelial tissue.

As used herein, "myelomonocytic tumor" refers to a tumor or cancer that is present and/or originated from myelomonocyte.

As used herein, "neural cell adhesion molecule L1 (NCAM L1)" refers to a neural cell adhesion molecule that belongs to the IgSF superfamily. Preferably, NCAM L1 has 6 immunoglobulin like domains and has 5 fibronectin type III like domains, and is a membrane-penetrating type glycoprotein expected to penetrate the membrane at a region having sufficient number, e.g., 23, hydrophobic amino acid residues starting with an amino acid with a small side chain, e.g., glycine (EP 0,572,664 A1; and Moos et al., *Nature*, 334: 701–703 (1988)). It is intended that NCAM L1 includes those variants with conservative amino acid substitutions that do not substantially alter its activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Bejacmin/Cummings Pub. co., p.224).

As used herein, "assessing" refers to quantitative and/or qualitative determination of the presence or quantity a NCAM L1 protein or a derivative or fragment thereof, or a mRNA encoding said NCAM L1 protein or a derivative or fragment thereof, e.g., obtaining an absolute value for the amount or concentration of the NCAM L1 protein or mRNA species, and also of obtaining an index, ratio, percentage, visual or other value indicative of the level of the NCAM L1 protein or mRNA species. Assessment may be direct or indirect and the chemical species actually detected need not of course be the NCAM L1 protein or mRNA species itself but may, for example, be a derivative thereof or some further substance.

As used herein, "antibody" includes polyclonal or monoclonal antibodies, single-chain antibodies and other antibody fragments, such as Fab fragments, which are composed of a light chain and the variable region of a heavy chain.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "blood" refers to the "circulating tissue" of the body; the fluid and its suspended formed elements that are circulated through the heart, arteries, capillaries, and veins. "Blood" also refers to the means by which 1) oxygen and nutritive materials are transported to the tissues, and 2) carbon dioxide and various metabolic products are removed for excretion. Blood consists of a pale yellow or gray-yellow fluid, plasma, in which are suspended red blood cells (erythrocytes), white blood cells (leukocytes) and platelets.

As used herein, "whole blood" refers to the blood drawn from a selected donor and may contain an anticoagulant such as citrate ion, heparin or EDTA.

As used herein, "serum" refers to the fluid portion of the blood obtained after removal of the fibrin clot and blood cells, distinguished from the plasma in circulating blood.

As used herein, "plasma" refers to the fluid, noncellular portion of the blood, distinguished from the serum obtained after coagulation.

For clarity of disclosure, and not by way of limitation, the detailed description of the invention is divided into the subsections that follow.

B. Methods for Prognosing or Diagnosing Vasculopathies

In one aspect, the invention is directed to a method for prognosing or diagnosing a vasculopathy in a mammal, which method comprises: a) assessing a NCAM L1 protein or a derivative or fragment thereof, or a mRNA encoding said NCAM L1 protein or a derivative or fragment thereof, in a mammal having or suspected of having a vasculopathy; b) assessing said NCAM L1 protein or a derivative or fragment thereof, or said mRNA encoding said NCAM L1 protein or a derivative or fragment thereof, in a mammal not having said vasculopathy; and c) comparing the presence or quantity of said NCAM L1 protein or mRNA assessed in steps a) and b), whereby said NCAM L1 protein or mRNA assessed in step a) is more than that assessed in step b) indicates the presence of said vasculopathy in said mammal.

The present method can be used in the prognosis and diagnosis of any type(s) of vasculopathy. Preferably, the method is used in the prognosis and diagnosis of a vasculitis, including a small, medium and large vessel vasculitis. More preferably, the method is used in the prognosis and diagnosis of a small vessel vasculitis.

Exemplary small vessel vasculitises include cutaneous vasculitis, e.g., idiopathic cutaneous vasculitis, urticarial vasculitis, leukocytoclastic vasculitis, livedo vasculitis, nodular vasculitis, Wegener's granulomatosis, Churg-Strauss syndrome, microscopic polyangiitis (microscopic polyarteritis), Henoch-Schönlein purpura, essential cryoglubulinemic vasculitis, and cutaneous leukocytoclastic angiitis. Exemplary medium vessel vasculitises include polyarteritis nodosa (classic polyarteritis nodosa) and Kawasaki disease. Exemplary large vessel vasculitises include giant cell (temporal) arteritis and Takayasu's arteritis.

The NCAM L1 protein or its mRNA can be assessed in vivo or in vitro. For example, the NCAM L1 protein or its mRNA contained in a sample, e.g., serum sample, collected from the mammal is assessed. Alternatively, vascular expression of the NCAM L1 protein or its mRNA can be assessed by an in situ detection method. Vascular expression of the NCAM L1 protein or its mRNA localized to endothelial cells can also be assessed.

Besides the prognosis and diagnosis, the present method can be used for monitoring treatment of the vasculopathy in the mammal. Preferably, the level of NCAM L1 protein or a derivative or fragment thereof, or a mRNA encoding said NCAM L1 protein or a derivative or fragment thereof, is quantified and the quantified level is used for assessing the degree or extent of the vasculopathy.

Any NCAM L1 protein or its mRNA or derivatives or fragments thereof can be used as the prognostic or diagnostic markers in the present methods. For example, NCAM L1 proteins with the following GenBank accession numbers can be used as the prognostic or diagnostic markers: T30532 (Fugu rubripes); T30581 (zebra fish); S36126 (rat); A43425 (chicken); S05479 (mouse); A41060 (human); NP_032504 (Mus musculus); NP_006605 (close homologue of L1 sapiens); NP_000416 (Homo sapiens); AAF22153 (Mus musculus); CAB57301 (Mus musculus); P32004 (HUMAN);

Q05695 (RAT); P11627 (MOUSE); AAD28610 (Cercopithecus aethiops); CAB37831 (Homo sapiens); AAC51746 (Homo sapiens); AAC15580 (Fugu rubripes); AAC14352 (Homo sapiens); CAA96469 (Fugu rubripes); CAA82564 (Homo sapiens); CAA41576 (Homo sapiens); 1411301A; CAA42508 (Homo sapiens); CAA41860 (Rattus norvegicus); AAA99159 (Carassius auratus); CAA61491 (Danio rerio); CAA61490 (Danio rerio); AAA59476 (Homo sapiens); AAA36353 (Homo sapiens).

Similarly, nucleic acids encoding NCAM L1 proteins with the following GenBank accession numbers can be used as the prognostic or diagnostic markers: AC005775 (Homo sapiens); AC 004690 (Homo sapiens); M28231 (Drosophila melanogaster neuroglian precursor); AH006326 (Drosophila melanogaster neuroglian (nrg), alternative splice products); AF050085 (Drosophila melanogaster neuroglian (nrg) gene; AF172277 (Homo sapiens); AF133093 (Mus musculus); AJ239325 (Homo sapiens); AL021940 (Homo sapiens); AF129167 (Chlorocebus aethiops); AJ011930 (Homo sapiens); U52112 (Homo sapiens); M97161 (Rattus norvegicus); AC005626 (Homo sapiens); AF026198 (Fugu rubripes); M77640 (Homo sapiens); U55211 (Carassius auratus); M74387 (Human).

The NCAM L1 protein or its mRNA or derivatives or fragments thereof can be assessed by any methods known in the art. For protein detection, the physical, chemical or biological properties of the NCAM L1 protein, such as gel mobility, chromatography characteristics, ligand binding affinity or specificity, or bioactivity can be used in the assay (See generally, *Current Protocols in Molecular Biology* (1998) § 20, John Wiley & Sons, Inc.). Preferably, immunological assays such as ELISA, Western blotting, immunofluoresence or immunoprecipitation can be used. For mRNA detection, Northern blotting, in situ hybridization or RNA sequencing can be used (Id.).

The NCAM L1 protein or its mRNA can be assessed in vivo or in vitro. Preferably, NCAM L1 protein or its mRNA in a biosample derived from a mammal is assessed in vitro. For example, NCAM L1 protein or its mRNA in a blood sample, e.g., serum, plasma or whole blood sample, can be assessed.

Any sample can be assayed for NCAM L1 protein or its mRNA using the above-described methods. In one embodiment, the sample being assayed is a biological sample from a mammal, particularly a human, such as a biological fluid or a biological tissue. Biological fluids, include, but are not limited to, urine, blood, plasma, serum, saliva, semen, stool, sputum, hair and other keratinous samples, cerebral spinal fluid, tears, mucus and amniotic fluid. Biological tissues contemplated include, but are not limited to, aggregates of cells, usually of a particular kind together with their intercellular substance that form one of the structural materials of a human, animal, plant, bacterial, fungal or viral structure, including connective, epithelium, muscle and nerve tissues, organs, tumors, lymph nodes, arteries and individual cell(s). In one specific embodiment, the body fluid to be assayed is urine. In another embodiment, the body fluid to be assayed is blood. Preferably, the blood sample is further separated into a plasma or serum fraction.

Serum or plasma can be recovered from the collected blood by any methods known in the art. In one specific embodiment, the serum or plasma is recovered from the collected blood by centrifugation. Preferably, the centrifugation is conducted in the presence of a sealant having a specific gravity greater than that of the serum or plasma and less than that of the blood corpuscles which will form the lower, whereby upon centrifugation, the sealant forms a separator between the upper serum or plasma layer and the lower blood corpuscle layer. The sealants that can be used in the processes include, but are not limited to, styrene resin powders, pellets or plates of a hydrogel of a crosslinked polymer of 2-hydroxyethyl methacrylate or acrylamide (U.S. Pat. No. 3,647,070), beads of polystyrene bearing an antithrombus agent or a wetting agent on the surfaces (U.S. Pat. No. 3,464,890) and a silicone fluid (U.S. Pat. Nos. 3,852,194 and 3,780,935). In a preferred embodiment, the sealant is a polymer of unsubstituted alkyl acrylates and/or unsubstituted alkyl methacrylates, the alkyl moiety having not more than 18 carbon atoms, the polymer material having a specific gravity of about 1.03 to 1.08 and a viscosity of about 5,000 to 1,000,000 cps at a shearing speed of about 1 second$^{-1}$ when measured at about 25° C. (U.S. Pat. No. 4,140,631).

In another specific embodiment, the serum or plasma is recovered from the collected blood by filtration. Preferably, the blood is filtered through a layer of glass fibers with an average diameter of about 0.2 to 5μ and a density of about 0.1 to 0.5 g./cm$^3$, the total volume of the plasma or serum to be separated being at most about 50% of the absorption volume of the glass fiber layer; and collecting the run-through from the glass fiber layer which is plasma or serum (U.S. Pat. No. 4,477,575). Also preferably, the blood is filtered through a layer of glass fibers having an average diameter 0.5 to 2.5μ impregnated with a polyacrylic ester derivative and polyethylene glycol (U.S. Pat. No. 5,364,533). More preferably, the polyacrylic ester derivative is poly(butyl acrylate), poly(methyl acrylate) or poly(ethyl acrylate), and (a) poly(butyl acrylate), (b) poly(methyl acrylate) or poly(ethyl acrylate) and (c) polyethylene glycol are used in admixture at a ratio of (10–12):(1–4):(1–4).

In still another specific embodiment, the serum or plasma is recovered from the collected blood by treating the blood with a coagulant containing a lignan skeleton having oxygen-containing side chains or rings (U.S. Pat. No. 4,803,153). Preferably, the coagulant contains a lignan skeleton having oxygen-containing side chains or rings, e.g., d-sesamin, 1-sesamin, paulownin, d-asarinin, 1-asarinin, 2α-paulownin, 6α-paulownin, pinoresinol, d-eudesmin, 1-pinoresinol β-D-glucoside, 1-pinoresinol, 1-pinoresinol monomethyl ether β-D-glucoside, epimagnolin, lirioresinol-B, syringaresinol (dl), lirioresinonB-dimethyl ether, phillyrin, magnolin, lirioresinol-A, 2α, 6α-d-sesamin, d-diaeudesmin, lirioresinol-C dimethyl ether (ddiayangambin) and sesamolin. More preferably, the coagulant is used in an amount ranging from about 0.01 to 50 g per 1 l of the blood.

In a specific embodiment, the NCAM L1 protein or its mRNA is assessed by an in situ detection method. Any in situ detection method can be used (See generally, *Current Protocols in Molecular Biology* (1998) § 20, John Wiley & Sons, Inc.). For example, immunofluorescence can be sued for in situ detection of NCAM L1 protein species and in situ hybridization can be used for in situ detection of NCAM L1 mRNA species. Preferably, the NCAM L1 protein or its mRNA localized between endothelial cells or on their luminal surface is assessed.

Any mammals such as, mice, rats, rabbits, cats, dogs, pigs, cows, ox, sheep, goats, horses, monkeys and other non-human primates can be tested by the present method. Preferably, a human is tested by the present method.

C. Methods for Prognosing or Diagnosing Neuroectodermal, Epithelial or Myelomonocytic Tumors In another aspect, the invention is directed to a method for prognosing or diagnosing a neuroectodermal, epithelial, myelomonocytic or lymphoid tumor in a mammal, which method comprises: a) assessing a NCAM L1 protein or a derivative or fragment thereof, or a mRNA encoding said NCAM L1 protein or a derivative or fragment thereof, in a mammal having or suspected of having a neuroectodermal, epithelial, myelomonocytic or lymphoid tumor; b) assessing said NCAM L1 protein or a derivative or fragment thereof, or said mRNA encoding said NCAM L1 protein or a derivative or fragment thereof, in a mammal not having said neuroectodermal, epithelial, myelomonocytic or lymphoid tumor; and c) comparing the presence or quantity of said NCAM L1 protein or mRNA assessed in steps a) and b), whereby said NCAM L1 protein or mRNA assessed in step a) is more than that assessed in step b) indicates the presence of said neuroectodermal, epithelial, myelomonocytic or lymphoid tumor in said mammal.

Any form of neuroectodermal tumor, epithelial tumor and myelomonocytic tumor that expresses NCAM L1, can be prognosed or diagnosed using the present method. For example, neuroectodermal tumor, such as melanoma, neuroblastoma or medullblastoma, epithelial tumor, such as renal and lung carcinoma, myelomonocytic tumor, such as myelomonocytic leukemia or lymphoid tumor, such as lymphoma, can be prognosed or diagnosed.

Any NCAM L1 protein or its mRNA or derivatives or fragments thereof can be used as the prognostic or diagnostic markers in the present methods. Preferably, the NCAM L1 protein being assessed is a soluble NCAM L1 protein.

Besides the prognosis and diagnosis, the present method can be used for monitoring treatment of the neuroectodermal, epithelial or myelomonocytic tumor in the mammal. Preferably, the level of NCAM L1 protein or a derivative or fragment thereof, or a mRNA encoding said NCAM L1 protein or a derivative or fragment thereof, is quantified and the quantified level is used for assessing the tumor burden and/or response to the tumor treatment.

The NCAM L1 protein or its mRNA or derivatives or fragments thereof can be assessed by any methods known in the art. For protein detection, the physical, chemical or biological properties of the NCAM L1 protein, such as gel mobility, chromatography characteristics, ligand binding affinity or specificity, or bioactivity can be used in the assay (See generally, *Current Protocols in Molecular Biology* (1998) § 20, John Wiley & Sons, Inc.). Preferably, Immunological assays such as ELISA, Western blotting, immunofluorescence or immunoprecipitation can be used. For mRNA detection, Northern blotting, in-situ hybridization or RNA sequencing can be used (Id.). Any NCAM L1 protein or its mRNA, including the ones described in the above Section B, can be used as the prognostic or diagnostic markers.

The NCAM L1 protein or its mRNA can be assessed in vivo or in vitro. Preferably, NCAM L1 protein or its mRNA in a biosample is collected and is assessed in vitro. For example, NCAM L1 protein or its mRNA in a blood sample, e.g., serum, plasma or whole blood sample, can be assessed. Any forms of samples and known sample collection methods, including the ones described in the above Section B, can be used in the present method.

Any mammals such as, mice, rats, rabbits, cats, dogs, pigs, cows, ox, sheep, goats, horses, monkeys and other non-human primates can be tested by the present method. Preferably, a human is tested by the present method.

The following example is included for illustrative purposes only and is not intended to limit the scope of the invention.

D. Examples

Figure 1:
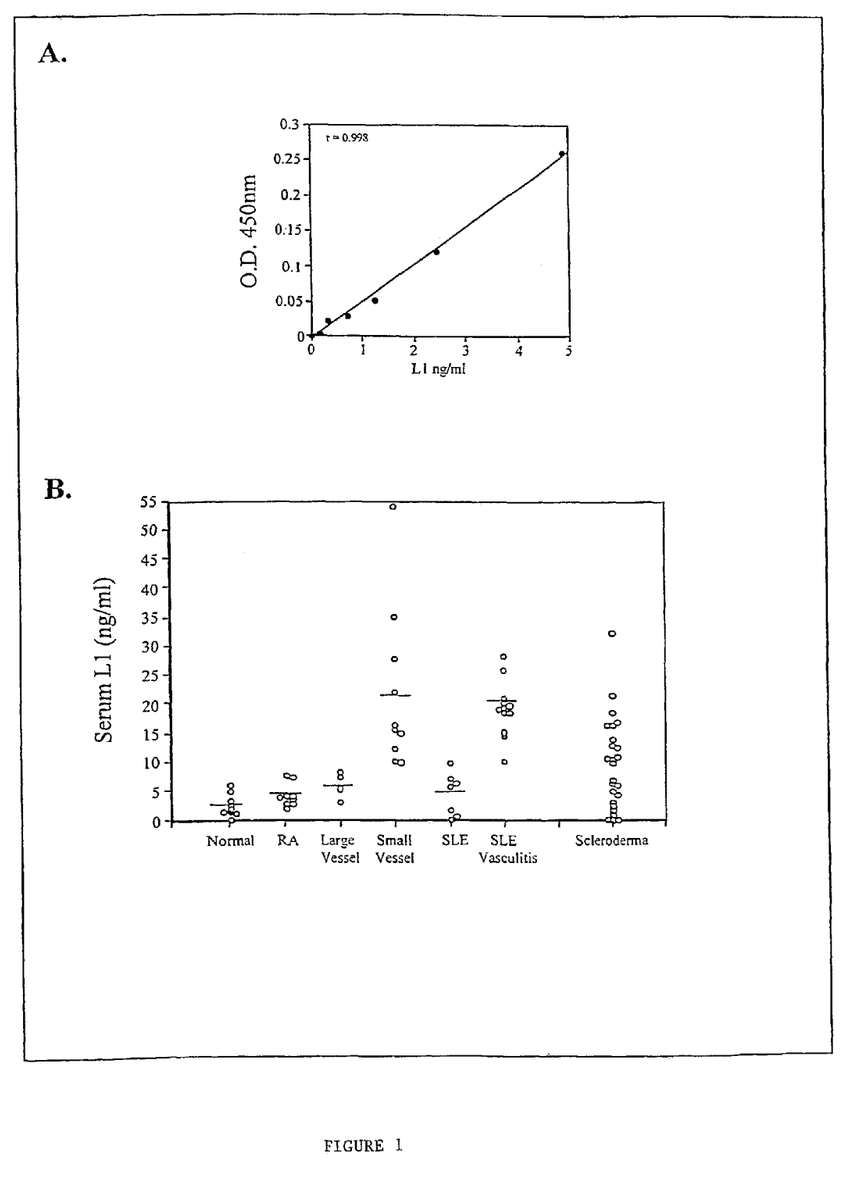

We have developed a sensitive quantitative two-antibody sandwich immunoassay which may have significant clinical utility as a diagnostic/prognostic kit both for certain vascular diseases and for certain cancers. This assay is designed to detect the neural cell adhesion molecule L1 in serum samples. The assay can preferably detect L1 in the linear range of 0.2–5 ng/ml (see FIG. 1A).

Detection of Vascular Diseases

In normal serum, L1 levels detected were in the range of 1–5 ng/ml (see FIG. 1B and Table 1). However, significantly elevated levels of L1 were detected in the serum of patients with small vessel vasculitis (idiopathic cutaneous vasculitis or urticarial vasculitis) and also in lupus (SLE) patients manifesting small vessel disease (FIG. 1B). Levels detected were significantly higher than those observed in normal serum, serum from patients with rheumatoid arthritis, or in patients with lupus but with no evidence of vasculitis (FIG. 1B). L1 levels between normal serum and a limited group of serum samples from patients with large vessel disease (giant cell arteritis) were not significantly different either reflecting specificity for vessel size or bed or simply the extent of vascular involvement (FIG. 1B). Elevated L1 levels were also detected in a subset of patients with scleroderma, a connective tissue disease with an episode of vascular involvement. These levels did not correlate with CRP levels (Not Shown) arguing against L1 being a marker of an acute phase reaction.

TABLE 1

Enzyme-linked iemmunoabsorbent assay to detect L1 in serum

|  | RA | large | Small | SLE | +vasculitis |
|---|---|---|---|---|---|
| Normal | 0.0468 | 0.1615 | 0.0002 | 0.3603 | 0.0001 |
| RA |  | 0.6404 | 0.0002 | 0.6302 | 0.0001 |
| Large Vessel |  |  | 0.0022 | 0.0004 | 0.7167 |
| SLE |  |  |  |  | 0.0002 |

Statistical analysis was performed using the Kruskal-Wallis test were statistical significance is assigned to values <0.0024.

Figure 2:
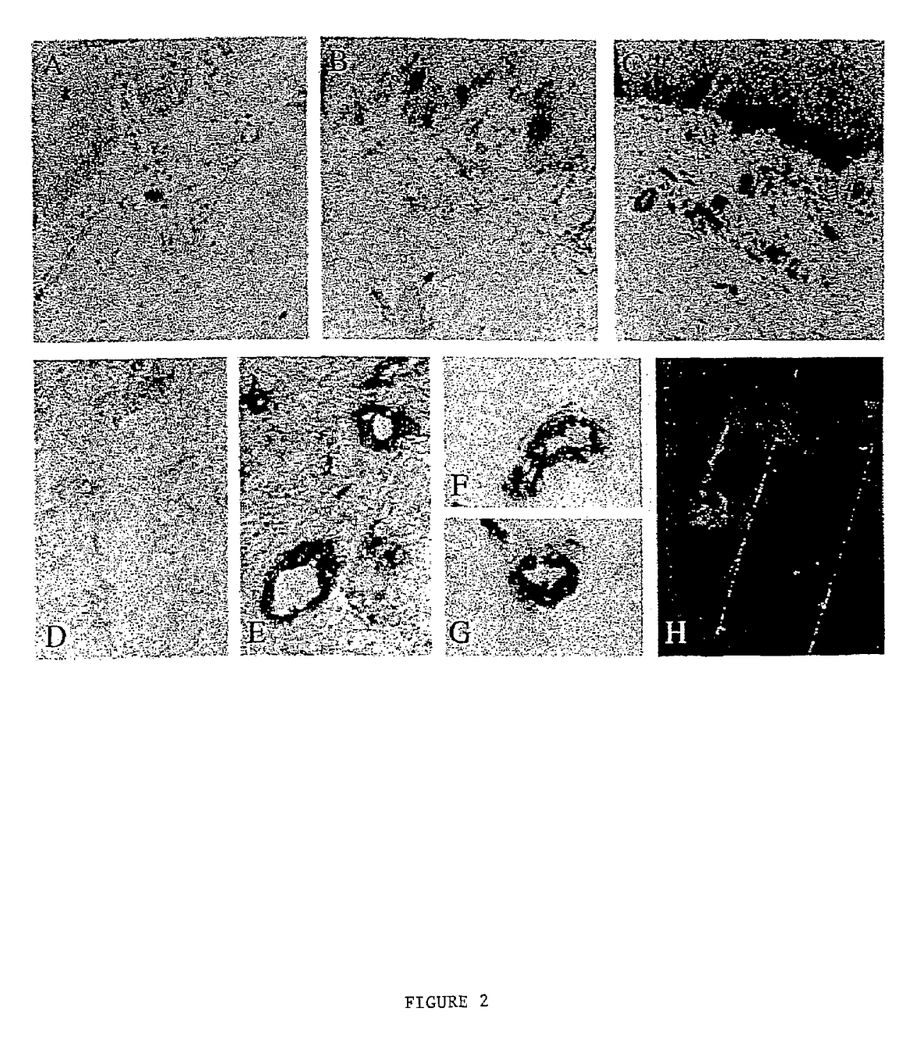

In situ staining of diseased vessels show that the increased L1 levels detected in the sera of patients with small vessel vasculitis maybe due to the de novo expression of L1 by diseased blood vessels (endothelial cells) (see FIG. 2). The presence of L1 in the serum maybe the result of posttranslational L1 cleavage or shedding into the blood stream. In this regard, L1 is sensitive to cleavage by both serine proteases and certain ADAMS.

The induction of L1 expression is presumed to be due to endothelial cell damage and/or activation. To our knowledge, there is currently no reliable serological test that can solely detect or measure endothelial cell damage/activation in vascular disease. Such a test would have significant clinical utility for prognosis and for measuring responses to different therapeutic modalities.

Detection of Tumors

L1 is highly expressed by a wide variety of cancers of different histological origin including neuroectodermal tumors, e.g., melanoma and neuroblastoma and epithelial tumors, e.g., renal and lung carcinomas, and tumor lines of myelomonocytic origin. L1 is shed from the surface of these tumors as a result of posttranslational cleavage.

Figure 3:
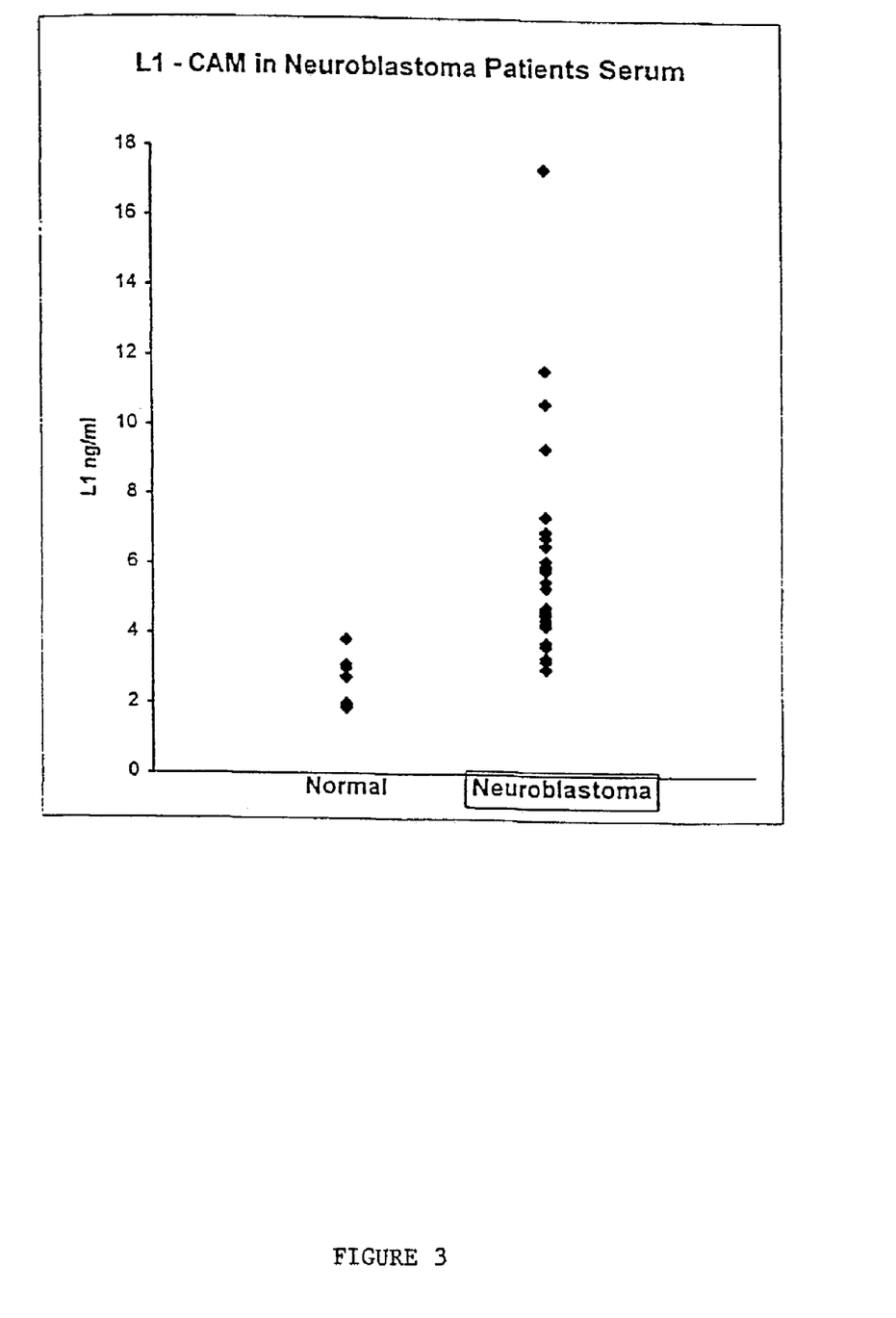
FIG. 3 depicts detection of L1-CAM in neuroblastoma patients serum.

We have determined that the levels of L1 in the sera of patients with neuroblastoma is significantly elevated above that in normal sera (see FIG. 3). Based on these findings we propose that the serological detection of L1 will also allow for the assessment of tumor burden and/or metastasis in L1+ tumors and providing a means for assessing the effectiveness of therapy.

Since modifications will be apparent to those of skill in this art, it is intended that this invention be limited only by the scope of the appended claims.

The invention claimed is:

1. A method for diagnosing vasculitis associated with overexpression of NCAM L1 in a mammal, comprising:
   a) assessing an expression level of a NCAM L1 protein or a mRNA encoding said NCAM L1 protein in the mammal; and
   b) comparing said level to an expression level of said NCAM L1 protein or said mRNA encoding said NCAM L1 protein in a mammal not having said vasculitis wherein an increase in the expression level indicates the presence of said vasculitis in said mammal.

2. The method of claim 1, wherein the NCAM L1 protein or its mRNA contained in a sample collected from the mammal is assessed.

3. The method of claim 2, wherein the sample is a serum sample.

4. The method of claim 1, wherein expression of the NCAM L1 protein or its mRNA is assessed by an in situ detection method.

5. The method of claim 4, wherein expression of the NCAM L1 protein or its mRNA is localized to endothelial cells.

6. The method of claim 1, wherein the mammal is a human.

7. The method of claim 1, which is used for monitoring treatment of the vasculitis in the mammal.

8. The method of claim 1, wherein the expression level of the NCAM L1 protein the mRNA encoding said NCAM L1 protein, is quantified and the quantified level is used for assessing the degree or extent of the vasculitis.

* * * * *